US012635930B2

(12) United States Patent
Amos et al.

(10) Patent No.: US 12,635,930 B2
(45) Date of Patent: May 26, 2026

(54) DETECTING ATRIAL FIBRILLATION AND ATRIAL FIBRILLATION TERMINATION

(71) Applicant: Biosense Webster (Israel) Ltd., Yokneam (IL)

(72) Inventors: Yariv Avraham Amos, Tzorit (IL); Matityahu Amit, Cohav-Yair zur-Yigal (IL); Stanislav Goldberg, Haifa (IL); Lior Botzer, Timrat (IL); Jonathan Yarnitsky, Haifa (IL); Elad Nakar, Timrat (IL); Eliyahu Ravuna, Kiryat Ata (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1102 days.

(21) Appl. No.: 17/342,321

(22) Filed: Jun. 8, 2021

(65) Prior Publication Data

US 2021/0391082 A1    Dec. 16, 2021

Related U.S. Application Data

(60) Provisional application No. 63/039,291, filed on Jun. 15, 2020.

(51) Int. Cl.
*A61B 5/36* (2021.01)
*A61B 5/00* (2006.01)
(Continued)

(52) U.S. Cl.
CPC .............. *A61B 5/361* (2021.01); *A61B 5/367* (2021.01); *A61B 5/7264* (2013.01); *G06N 3/044* (2023.01); *G06N 3/08* (2013.01); *G06V*

*10/443* (2022.01); *G16H 50/20* (2018.01); *A61B 2018/00577* (2013.01); *A61B 2018/00839* (2013.01)

(58) Field of Classification Search
None
See application file for complete search history.

(56) References Cited

U.S. PATENT DOCUMENTS 7,963,925 B1 *  6/2011  Schecter .............. A61B 5/0031
                                                                600/527
10,517,496 B2  12/2019  Urman et al.
(Continued)

OTHER PUBLICATIONS

Miyasaka et al., "Secular trends in incidence of atrial fibrillation in Olmsted County, Minnesota, 1980 to 2000, and Implications on the projections for future prevalence." Circulation vol. 114,2 (2006).
(Continued)

*Primary Examiner* — Ankit D Tejani
(74) *Attorney, Agent, or Firm* — Volpe Koenig

(57) ABSTRACT

A method is provided. The method is implemented by a detection engine embodied in processor executable code stored on a memory and executed by at least one processor. The method includes modeling a vector velocity field that measures and quantifies a velocity of electrocardiogram data signals that pass through a local activation time. The method further includes determining codes for each point in plane to provide a color code vector field image; detecting focal and rotor indications by using kernels to scan the color coded vector field image; and classifying the focal and rotor indications into perpetuators.

18 Claims, 9 Drawing Sheets

(51) Int. Cl.

| | |
|---|---|
| *A61B 5/361* | (2021.01) |
| *A61B 5/367* | (2021.01) |
| *G06N 3/044* | (2023.01) |
| *G06N 3/08* | (2023.01) |
| *G06V 10/44* | (2022.01) |
| *G16H 50/20* | (2018.01) |
| *A61B 18/00* | (2006.01) |

(56) References Cited

U.S. PATENT DOCUMENTS

| | | | |
|---|---|---|---|
| 2017/0065198 A1* | 3/2017 | Ruppersberg | A61B 5/341 |
| 2017/0202521 A1 | 7/2017 | Urman et al. | |
| 2019/0090774 A1* | 3/2019 | Yang | A61B 5/303 |
| 2019/0223819 A1* | 7/2019 | Mansi | G06T 15/205 |

OTHER PUBLICATIONS

Colilla et al. "Estimates of current and future incidence and prevalence of atrial fibrillation in the U.S. adult population." The American journal of cardiology vol. 112,8 (2013).

Chugh et al., "Worldwide Epidemiology of Atrial Fibrillation - A Global Burden of Disease 2010 Study," Circulation, vol. 129, Issue 8 (Feb. 25, 2014).

Lin et al., "Benefits of Atrial Substrate Modification Guided by Electrogram Similarity and Phase Mapping Techniques to Eliminate Rotors and Focal Sources Versus Conventional Defragmentation in Persistent Atrial Fibrillation," JACC: Clinical Electrophysiology. (2016).

Bellmann et al., "Velocity characteristics of atrial fibrillation sources determined by electrographic flow mapping before and after catheter ablation," International journal of cardiology 286, 56-60 (2019).

Masè et al., "Velocity Field Analysis of Activation Maps in Atrial Fibrillation a Simulation Study," In: Dossel O., Schlegel W.C. (eds) World Congress on Medical Physics and Biomedical Engineering, Sep. 7-12, 2009, Munich, Germany. IFMBE Proceedings, vol. 25/4. Springer, Berlin, Heidelberg (2009).

Cantwell et al., "Techniques for automated local activation time annotation and conduction velocity estimation in cardiac mapping," Computers in Biology and Medicine (2015).

Gonzalo et al., "Real-Time Rotational Activity Detection in Atrial Fibrillation." Frontiers in physiology vol. 9 208. (Mar. 13, 2018).

Ganesan et al., "Locating Atrial Fibrillation Rotor and Focal Sources Using Iterative Navigation of Multipole Diagnostic Catheters." Cardiovascular engineering and technology vol. 10,2: 354-366 (2019).

Extended European Search Report dated Nov. 10, 2021 for European Patent Application No. 21179298.1.

Chinese Office Action dated May 23, 2025 for Chinese Patent Application No. 202110660574.1.

Hannun, A.Y., Rajpurkar, P., Haghpanahi, M. et al. Cardiologist-level arrhythmia detection and classification in ambulatory electrocardiograms using a deep neural network. Nat Med 25, 65-69 (2019).

Communication pursuant to Article 298.1 94(3) EPC dated Oct. 1, 2025 for European Patent Application No. 21 179 298.1.

* cited by examiner

SYSTEM
200

METHOD
300

DETECT SEGMENT
307

DETERMINE FIELD
315

COLOR CODE IMAGE
330

DETERMINE AND
CALSSIFY
PERPETUATORS
321

DETECT THE INDICATIONS
345

MARK PERPETUATORS
360

CLASSIFY THE INDICATIONS INTO
THE PERPETUATORS
375

METHOD
600

RECEIVE INPUT
605

DETECT A SEGMENT OF LAT
610

DETERMINE VECTOR VELOCITY FIELD
625

COLOR CODE VECTOR FIELD IMAGE
630

DETECT FOCAL/ROTOR INDICATIONS
645

MARK PERPETUATORS
660

CLASSIFY THE FOCAL/ROTOR INDICATIONS
INTO THE PERPETUATORS
675

DETECTING ATRIAL FIBRILLATION AND ATRIAL FIBRILLATION TERMINATION

PRIORITY CLAIM

The application claims priority from U.S. Provisional Patent Application Ser. No. 63/039,291, entitled "ATRIAL FIBRILLATION," which is hereby incorporated by reference as if set forth full in this application for all purposes.

FIELD OF INVENTION

The present invention is related to artificial intelligence and machine learning associated with atrial fibrillation. More particularly, the present invention relates to a system and method implementing a machine learning/artificial intelligence algorithm for detecting atrial fibrillation and atrial fibrillation termination.

BACKGROUND

Atrial fibrillation ("aFib") is a quivering or irregular heartbeat (arrhythmia) that can lead to blood clots, stroke, heart failure, and other heart-related complications. aFib is the most common arrhythmia diagnosed in clinical practice. Estimates of the prevalence of aFib in the United States ranges from about 2.7 million to 6.1 million and is expected to rise to 12.1 million in 2030. Worldwide estimates estimate the number of individuals with aFib in 2010 at approximately 33.5 million, according to a 2013 study. This represents about 0.5 percent of the world's population.

At present, physicians are unable to determine whether and when a specific aFib case was terminated successfully from a set of electrocardiogram (ECG) signals. For instance, conventional mechanisms discuss phase mapping (i.e., calculating the delays between electrodes and finding a phase singularity) and vector analysis without using a velocity vector field, machine learning, deep learning, and/or other detailed algorithms. At best, conventional mechanisms may use velocity characteristics of aFib sources determined by electrographic flow mapping before and after catheter ablation, yet these conventional mechanisms still fail to differentiate between active and passive focal sources. In turn, conventional mechanisms fall short of determining aFib termination.

SUMMARY

According to an exemplary embodiment, a method is provided. The method is implemented by a detection engine embodied in processor executable code stored on a memory and executed by at least one processor. The method includes modeling a vector velocity field that measures and quantifies a velocity of electrocardiogram data signals that pass through a local activation time. The method further includes determining one or more codes for each point in plane to provide a color code vector field image; detecting focal and rotor indications by using one or more kernels to scan the color coded vector field image; and classifying the focal and rotor indications into perpetuators.

According to one or more embodiments, the exemplary method embodiment above can be implemented as an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
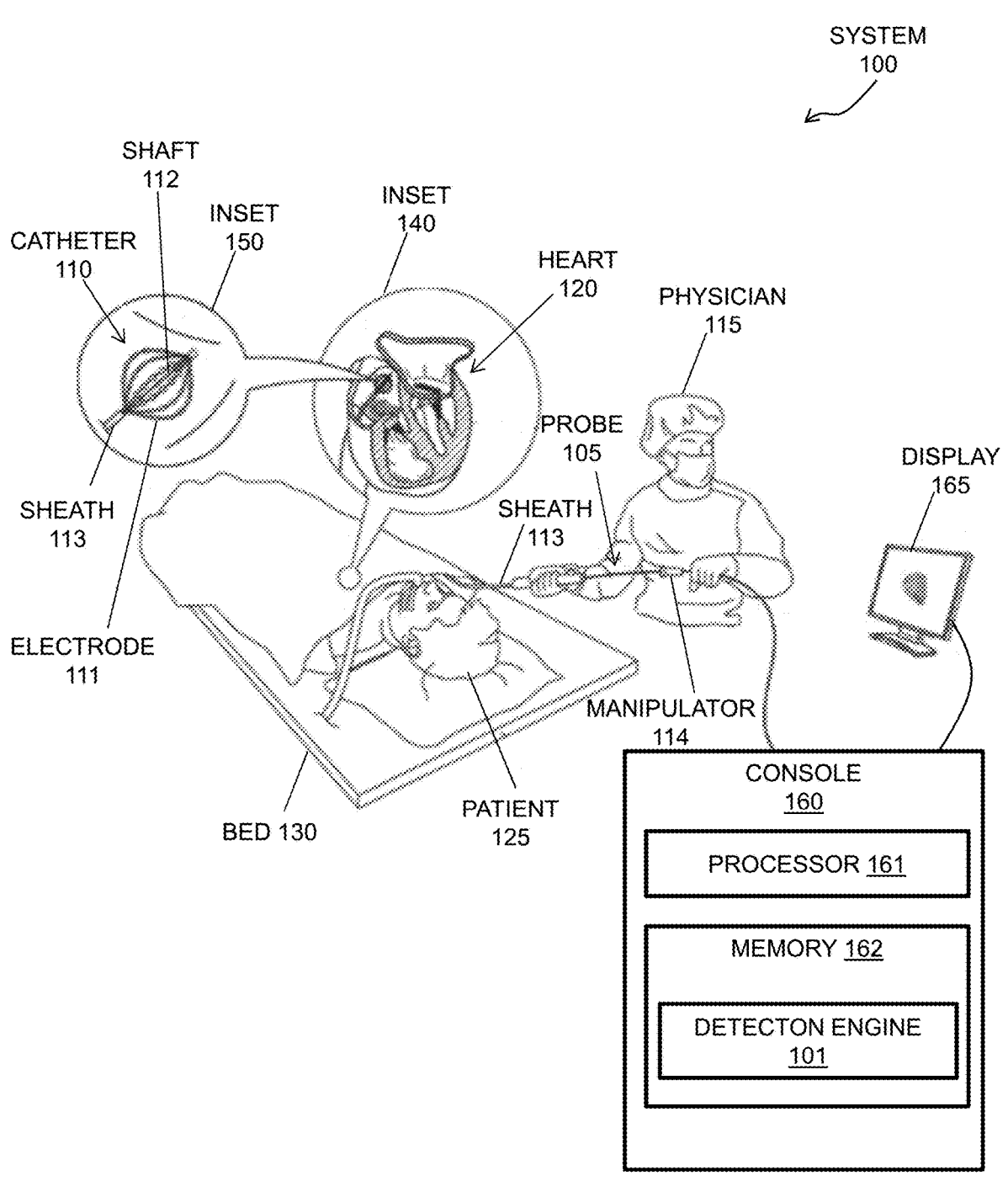
FIG. 1 illustrates a diagram of an exemplary system in which one or more features of the disclosure subject matter can be implemented according to one or more embodiments.

Disclosed herein is a machine learning and/or an artificial intelligence method and system implemented by a detection engine. More particularly, the present invention relates to a detection engine including a machine learning/artificial intelligence algorithm that detects aFib and aFib termination.

One or more advantages, technical effects, and/or benefits of the detection engine can include solving active versus passive questions (e.g., differentiate between focal sources and rotors) using a feedback loop based on actual ablation of focal activity, which otherwise is not available through conventional mechanisms. In this regard, the detection engine can model vector velocity field while differentiating between focal sources and rotors (e.g., active and passive). That is, the detection engine can define where to calculate local activation times (LATs), calculate a derivative of LAT to get velocity, identify focal sources (e.g., within 1 mm box), classify active or passive focal sources (e.g., in the 1 mm box), provide a retrospective analysis (e.g., investigate past cases and determine where ablation occurred), and provide a prospective analysis (e.g., determine where to ablate).

For ease of explanation, the detection engine is described herein with respect to determining and treating aFib respective to a heart; however, any anatomical structure, body part, organ, or portion thereof can be a target for mapping by the detection engine described herein. Further, the detection engine and/or the machine learning/artificial intelligence algorithm is a processor executable code or software that is necessarily rooted in process operations by, and in processing hardware of, medical device equipment.

According to one or more embodiments, a method implemented by a detection engine embodied in processor executable code stored on a memory and executed by at least one processor is provided. The method includes modeling, by the detection engine, a vector velocity field that measures and quantifies a velocity of electrocardiogram data signals that pass through a local activation time; determining, by the detection engine, one or more codes for each point in plane to provide a color code vector field image; detecting, by the detection engine, focal and rotor indications by using one or more kernels to scan the color coded vector field image; and classifying, by the detection engine, the focal and rotor indications into perpetuators.

According to one or more embodiments or any of the method embodiments herein, the electrocardiogram data signals can be detected by a catheter within an anatomical structure and in communication with the detection engine.

According to one or more embodiments or any of the method embodiments herein, the detection engine can detect one or more segments of the local activation time relative to a first activation time.

According to one or more embodiments or any of the method embodiments herein, the detection engine can model a vector velocity field by calculating a direction of an electrical wave at each x, y point and utilizing a derivative of a polynomial surface to provide the velocity vector field.

According to one or more embodiments or any of the method embodiments herein, the detection engine can classify the perpetuators by utilizing the velocity vector field as an input to a machine learning or artificial intelligence algorithm.

According to one or more embodiments or any of the method embodiments herein, the machine learning or artificial intelligence algorithm can include a deep convolutional neural network or a recurrent neural network to detect locations of gold standard perpetuators of the perpetuators.

According to one or more embodiments or any of the method embodiments herein, the machine learning or artificial intelligence algorithm can determine whether an outcome of an ablation of a specific case regarding the electrocardiogram data signals was successful or not.

According to one or more embodiments or any of the method embodiments herein, the focal and rotor indications can be detected when, within the one or more kernels, all directions are in order.

According to one or more embodiments or any of the method embodiments herein, the detection engine can automatically identify and annotate atrial fibrillation perpetuators based on vector velocity and ablation information when marking the perpetuators.

According to one or more embodiments or any of the method embodiments herein, region of interest annotations can be used by the detection engine with respect to active, passive, and unknown categories to indicate at least whether a region of interest was ablated or an atrial fibrillation terminated.

According to one or more embodiments, a system includes a memory storing processor executable code for a detection engine. The system also include at least one processor executing the processor executable code to cause the system to model, by the detection engine, a vector velocity field that measures and quantifies a velocity of electrocardiogram data signals that pass through a local activation time; determine, by the detection engine, one or more codes for each point in plane to provide a color code vector field image; detect, by the detection engine, focal and rotor indications by using one or more kernels to scan the color coded vector field image; and classify, by the detection engine, the focal and rotor indications into perpetuators.

According to one or more embodiments or any of the system embodiments herein, the electrocardiogram data signals can be detected by a catheter within an anatomical structure and in communication with the detection engine.

According to one or more embodiments or any of the system embodiments herein, the detection engine can detect one or more segments of the local activation time relative to a first activation time.

According to one or more embodiments or any of the system embodiments herein, the detection engine can model a vector velocity field by calculating a direction of an electrical wave at each x, y point and utilizing a derivative of a polynomial surface to provide the velocity vector field.

According to one or more embodiments or any of the system embodiments herein, the detection engine can classify the perpetuators by utilizing the velocity vector field as an input to a machine learning or artificial intelligence algorithm.

According to one or more embodiments or any of the system embodiments herein, the machine learning or artificial intelligence algorithm can include a deep convolutional neural network or a recurrent neural network to detect locations of gold standard perpetuators of the perpetuators.

According to one or more embodiments or any of the system embodiments herein, the machine learning or artificial intelligence algorithm can determine whether an outcome of an ablation of a specific case regarding the electrocardiogram data signals was successful or not.

According to one or more embodiments or any of the system embodiments herein, the focal and rotor indications can be detected when, within the one or more kernels, all directions are in order.

According to one or more embodiments or any of the system embodiments herein, the detection engine can automatically identify and annotate atrial fibrillation perpetuators based on vector velocity and ablation information when marking the perpetuators.

According to one or more embodiments or any of the system embodiments herein, region of interest annotations can be used by the detection engine with respect to active, passive, and unknown categories to indicate at least whether a region of interest was ablated or an atrial fibrillation terminated.

FIG. 1 is a diagram of an example system (e.g., medical device equipment), shown as a system 100, in which one or more features of the subject matter herein can be implemented according to one or more embodiments. All or part of the system 100 can be used to collect information (e.g., biometric data and/or a training dataset) and/or used to implement a detection engine 101 (e.g., a machine learning and/or an artificial intelligence algorithm) as described herein. The detection engine 101 can be defined as a deep learning optimization for detecting perpetuators of aFib to be ablated for treatment of persistent aFib subject and classifying velocity vector field images and raw data into the perpetuators.

The system 100, as illustrated, includes a probe 105 with a catheter 110 (including at least one electrode 111), a shaft 112, a sheath 113, and a manipulator 114. The system 100, as illustrated, also includes a physician 115 (or a medical professional or clinician), a heart 120, a patient 125, and a bed 130 (or a table). Note that insets 140 and 150 show the heart 120 and the catheter 110 in greater detail. The system 100 also, as illustrated, includes a console 160 (including one or more processors 161 and memories 162) and a display 165. Note further each element and/or item of the system 100 is representative of one or more of that element and/or that item. The example of the system 100 shown in FIG. 1 can be modified to implement the embodiments disclosed herein. The disclosed embodiments can similarly be applied using other system components and settings.

Additionally, the system 100 can include additional components, such as elements for sensing electrical activity, wired or wireless connectors, processing and display devices, or the like.

The system 100 can be utilized to detect, diagnose, and/or treat cardiac conditions (e.g., using the detection engine 101). Cardiac conditions, such as cardiac arrhythmias, persist as common and dangerous medical ailments, especially in the aging population. For instance, the system 100 can be part of a surgical system (e.g., CARTO® system sold by Biosense Webster) that is configured to obtain biometric data (e.g., anatomical and electrical measurements of a patient's organ, such as the heart 120) and perform a cardiac ablation procedure. More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 120. Such locating may be done via an electrophysiological investigation during which electrical potentials are detected spatially resolved with a mapping catheter (e.g., the catheter 110) introduced into the chamber of the heart 120. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time. In this case, the detection engine 101 can be directly stored and executed by the catheter 110.

In patients (e.g., the patient 125) with normal sinus rhythm (NSR), the heart (e.g., the heart 120), which includes atrial, ventricular, and excitatory conduction tissue, is electrically excited to beat in a synchronous, patterned fashion. Note that this electrical excitement can be detected as intracardiac electrocardiogram (IC ECG) data or the like.

The heart 120, in general, is made up of four chambers—two upper chambers (atria) and two lower chambers (ventricles). The coronary sinus (CS) is a collection of veins joined together to form a large vessel that collects blood from the heart muscle and delivers less-oxygenated blood to the right atrium. The rhythm of the heart 120 is normally controlled by the sinus node (not shown) located in the right atrium. The sinus node produces electrical impulses that normally start each heartbeat and acts as a natural pacemaker. From the sinus node, the electrical impulses travel across the atria, causing the atria muscles to contract and pump blood into the ventricles. The electrical impulses then arrive at a cluster of cells called the atrioventricular node (AV node) (not shown). The AV node is usually the only pathway for signals to travel from the atria to the ventricles. The AV node slows down the electrical signal before sending it to the ventricles. The delay, even though slight, allows the ventricles to fill with blood. When electrical impulses reach the muscles of the ventricles, the muscles contract, causing the muscles to pump blood either to the lungs or to the rest of the body. In a healthy heart 120, this process usually goes smoothly, resulting in a normal resting heart rate of 60 to 100 beats a minute. In a heart 120 that has one of the disease states identified above, faulty electrical connections in the heart or abnormal areas of electrical activity trigger and sustain an abnormal rhythm. When this happens, the heart rate accelerates too quickly and doesn't allow enough time for the heart 120 to fill before it contracts again. These ineffective contractions of the heart 120 may cause lightheadedness or dizziness because the brain may not be receiving enough blood and oxygen.

In patients (e.g., the patient 125) with a cardiac arrhythmia (e.g., atrial fibrillation or aFib), abnormal regions of cardiac tissue do not follow a synchronous beating cycle associated with normally conductive tissue, which is in contrast to patients with NSR. Instead, the abnormal regions of cardiac tissue aberrantly conduct to adjacent tissue, thereby disrupting the cardiac cycle into an asynchronous cardiac rhythm. Note that this asynchronous cardiac rhythm can also be detected as the IC ECG data. Such abnormal conduction has been previously known to occur at various regions of the heart 120, for example, in the region of the sino-atrial (SA) node, along the conduction pathways of the atrioventricular (AV) node, or in the cardiac muscle tissue forming the walls of the ventricular and atrial cardiac chambers. There are other conditions, such as flutter, where the pattern of abnormally conducting tissues lead to reentry paths such that the chamber beats in a regular pattern that can be multiple times the sinus rhythm.

In support of the system 100 detecting, diagnosing, and/or treating cardiac conditions, the probe 105 can be navigated by the physician 115 into the heart 120 of the patient 125 lying on the bed 130. For instance, the physician 115 can insert the shaft 112 through the sheath 113, while manipulating a distal end of the shaft 112 using the manipulator 114 near the proximal end of the catheter 110 and/or deflection from the sheath 113. As shown in an inset 140, the catheter 110 can be fitted at the distal end of the shaft 112. The catheter 110 can be inserted through the sheath 113 in a collapsed state and can be then expanded within the heart 120.

Generally, electrical activity at a point in the heart 120 may be typically measured by advancing the catheter 110 containing an electrical sensor at or near its distal tip (e.g., the at least one electrode 111) to that point in the heart 120, contacting the tissue with the sensor and acquiring data at that point. One drawback with mapping a cardiac chamber using a catheter type containing only a single, distal tip electrode is the long period of time required to accumulate data on a point-by-point basis over the requisite number of points required for a detailed map of the chamber as a whole. Accordingly, multiple-electrode catheters (e.g., the catheter 110) have been developed to simultaneously measure electrical activity at multiple points in the heart chamber.

The catheter 110, which can include the at least one electrode 111 and a catheter needle coupled onto a body thereof, can be configured to obtain biometric data, such as electrical signals of an intra-body organ (e.g., the heart 120), and/or to ablate tissue areas of thereof (e.g., a cardiac chamber of the heart 120). Note that the electrodes 111 are representative of any like elements, such as tracking coils, piezoelectric transducer, electrodes, or combination of elements configured to ablate the tissue areas or to obtain the biometric data. According to one or more embodiments, the catheter 110 can include one or more position sensors that used are to determine trajectory information. The trajectory information can be used to infer motion characteristics, such as the contractility of the tissue.

Biometric data (e.g., patient biometrics, patient data, or patient biometric data) can include one or more of local activation times (LATs), electrical activity, topology, bipolar mapping, reference activity, ventricle activity, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, IC ECG data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

For example, the catheter 110 can use the electrodes 111 to implement intravascular ultrasound and/or Mill catheterization to image the heart 120 (e.g., obtain and process the biometric data). Inset 150 shows the catheter 110 in an enlarged view, inside a cardiac chamber of the heart 120. Although the catheter 110 is shown to be a point catheter, it will be understood that any shape that includes one or more electrodes 111 can be used to implement the exemplary embodiments disclosed herein.

Examples of the catheter 110 include, but are not limited to, a linear catheter with multiple electrodes, a balloon catheter including electrodes dispersed on multiple spines that shape the balloon, a lasso or loop catheter with multiple electrodes, a contact-force sensing catheter, or any other applicable shape or type. Linear catheters can be fully or partially elastic such that it can twist, bend, and or otherwise change its shape based on received signal and/or based on application of an external force (e.g., cardiac tissue) on the linear catheter. The balloon catheter can be designed such that when deployed into a patient's body, its electrodes can be held in intimate contact against an endocardial surface. As an example, a balloon catheter can be inserted into a lumen, such as a PV. The balloon catheter can be inserted into the PV in a deflated state, such that the balloon catheter does not occupy its maximum volume while being inserted into the PV. The balloon catheter can expand while inside the PV, such that those electrodes on the balloon catheter are in contact with an entire circular section of the PV. Such contact with an entire circular section of the PV, or any other lumen, can enable efficient imaging and/or ablation.

According to other examples, body patches and/or body surface electrodes may also be positioned on or proximate to a body of the patient 125. The catheter 110 with the one or more electrodes 111 can be positioned within the body (e.g., within the heart 120) and a position of the catheter 110 can be determined by the 100 system based on signals transmitted and received between the one or more electrodes 111 of the catheter 110 and the body patches and/or body surface electrodes. Additionally, the electrodes 111 can sense the biometric data from within the body of the patient 125, such as within the heart 120 (e.g., the electrodes 111 sense the electrical potential of the tissue in real time). The biometric data can be associated with the determined position of the catheter 110 such that a rendering of the patient's body part (e.g., the heart 120) can be displayed and show the biometric data overlaid on a shape of the body part.

The probe 105 and other items of the system 100 can be connected to the console 160. The console 160 can include any computing device, which employs the machine learning and/or an artificial intelligence algorithm (represented as the detection engine 101). According to an exemplary embodiment, the console 160 includes the one or more processors 161 (any computing hardware) and the memory 162 (any non-transitory tangible media), where the one or more processors 161 execute computer instructions with respect the detection engine 101 and the memory 162 stores these instructions for execution by the one or more processors 161. For instance, the console 160 can be configured to receive and process the biometric data and determine if a given tissue area conducts electricity.

In some embodiments, the console 160 can be further programmed by the detection engine 101 (in software) to carry out the functions of modeling a vector velocity field that measures and quantifies a velocity of electrocardiogram data signals that pass through a local activation time; determining one or more codes for each point in plane to provide a color code vector field image; detecting focal and rotor indications by using one or more kernels (e.g., a space within a map) to scan the color coded vector field image; and classifying the focal and rotor indications into perpetuators. For instance, the detection engine 101 can include a deep learning optimization (described herein with respect to FIGS. 3 and 6), that receives biometric data acquired by the catheter 110 as it is maneuvered within the anatomical structure. Once the mappings are generated, the detection engine 101 can receive inputs representing user modifications of the mappings, such as through existing user interface and/or a specialized user interface of the detection engine 101. Generally, the detection engine 101 can provide one or more user interfaces, such as on behalf of the operating system or other application and/or directly as needed. The user interfaces include, but are not limited to, internet browsers, graphic user interfaces (GUIs), window interfaces, and/or other visual interfaces for applications, operating systems, file folders, and the like. According to one or more embodiments, the detection engine 101 can be external to the console 160 and can be located, for example, in the catheter 110, in an external device, in a mobile device, in a cloud-based device, or can be a standalone processor. In this regard, the detection engine 101 can be transferable/downloaded in electronic form, over a network.

In an example, the console 160 can be any computing device, as noted herein, including software (e.g., the detection engine 101) and/or hardware (e.g., the processor 161 and the memory 162), such as a general-purpose computer, with suitable front end and interface circuits for transmitting and receiving signals to and from the probe 105, as well as for controlling the other components of the system 100. For example, the front end and interface circuits include input/output (I/O) communication interfaces that enables the console 160 to receive signals from and/or transfer signals to the at least one electrode 111. The console 160 can include real-time noise reduction circuitry typically configured as a field programmable gate array (FPGA), followed by an analog-to-digital (A/D) ECG or electrocardiograph/electromyogram (EMG) signal conversion integrated circuit. The console 160 can pass the signal from an A/D ECG or EMG circuit to another processor and/or can be programmed to perform one or more functions disclosed herein.

The display 165, which can be any electronic device for the visual presentation of the biometric data, is connected to the console 160. According to an exemplary embodiment, during a procedure, the console 160 can facilitate on the display 165 a presentation of a body part rendering to the physician 115 and store data representing the body part rendering in the memory 162. For instance, maps depicting motion characteristics can be rendered/constructed based on the trajectory information sampled at a sufficient number of points in the heart 120. As an example, the display 165 can include a touchscreen that can be configured to accept inputs from the medical professional 115, in addition to presenting the body part rendering.

In some embodiments, the physician 115 can manipulate the elements of the system 100 and/or the body part rendering using one or more input devices, such as a touch pad, a mouse, a keyboard, a gesture recognition apparatus, or the like. For example, an input device can be used to change a position of the catheter 110, such that rendering is updated. Note that the display 165 can be located at a same location or a remote location, such as a separate hospital or in separate healthcare provider networks.

According to one or more embodiments, the system 100 can also obtain the biometric data using ultrasound, computed tomography (CT), MRI, or other medical imaging techniques utilizing the catheter 110 or other medical equipment. For instance, the system 100 can obtain ECG data and/or anatomical and electrical measurements of the heart 120 (e.g., the biometric data) using one or more catheters 110 or other sensors. More particularly, the console 160 can be connected, by a cable, to BS electrodes, which include adhesive skin patches affixed to the patient 125. The BS electrodes can procure/generate the biometric data in the form of the BS ECG data. For instance, the processor 161 can determine position coordinates of the catheter 110 inside the body part (e.g., the heart 120) of the patient 125. The position coordinates may be based on impedances or electromagnetic fields measured between the body surface electrodes and the electrode 111 of the catheter 110 or other electromagnetic components. Additionally, or alternatively, location pads, which generate magnetic fields used for navigation, may be located on a surface of the bed 130 and may be separate from the bed 130. The biometric data can be transmitted to the console 160 and stored in the memory 162. Alternatively, or in addition, the biometric data may be transmitted to a server, which may be local or remote, using a network as further described herein.

According to one or more exemplary embodiments, the catheter 110 may be configured to ablate tissue areas of a cardiac chamber of the heart 120. Inset 150 shows the catheter 110 in an enlarged view, inside a cardiac chamber of the heart 120. For instance, ablation electrodes, such as the at least one electrode 111, may be configured to provide energy to tissue areas of an intra-body organ (e.g., the heart 120). The energy may be thermal energy and may cause damage to the tissue area starting from the surface of the tissue area and extending into the thickness of the tissue area. The biometric data with respect to ablation procedures (e.g., ablation tissues, ablation locations, etc.) can be considered ablation data.

According to an example, with respect to obtaining the biometric data, a multi-electrode catheter (e.g., the catheter 110) can be advanced into a chamber of the heart 120. Anteroposterior (AP) and lateral fluorograms can be obtained to establish the position and orientation of each of the electrodes. ECGs can be recorded from each of the electrodes 111 in contact with a cardiac surface relative to a temporal reference, such as the onset of the P-wave in sinus rhythm from a BS ECG and/or signals from electrodes 111 of the catheter 110 placed in the coronary sinus. The system, as further disclosed herein, may differentiate between those electrodes that register electrical activity and those that do not due to absence of close proximity to the endocardial wall. After initial ECGs are recorded, the catheter may be repositioned, and fluorograms and ECGs may be recorded again. An electrical map (e.g., via cardiac mapping) can then be constructed from iterations of the process above.

Cardiac mapping can be implemented using one or more techniques. Generally, mapping of cardiac areas such as cardiac regions, tissue, veins, arteries and/or electrical pathways of the heart 120 may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping (which is an example of heart imaging) may include mapping based on one or more modalities such as, but not limited to LAT, local activation velocity, an electrical activity, a topology, a bipolar mapping, a dominant frequency, or an impedance. Data (e.g., biometric data) corresponding to multiple modalities may be captured using a catheter (e.g., the catheter 110) inserted into a patient's body and may be provided for rendering at the same time or at different times based on corresponding settings and/or preferences of the physician 115.

As an example of a first technique, cardiac mapping may be implemented by sensing an electrical property of heart tissue, for example, LAT, as a function of the precise location within the heart 120. The corresponding data (e.g., biometric data) may be acquired with one or more catheters (e.g., the catheter 110) that are advanced into the heart 1120 and that have electrical and location sensors (e.g., the electrodes 111) in their distal tips. As specific examples, location and electrical activity may be initially measured on about 10 to about 20 points on the interior surface of the heart 120. These data points may be generally sufficient to generate a preliminary reconstruction or map of the cardiac surface to a satisfactory quality. The preliminary map may be combined with data taken at additional points to generate a more comprehensive map of the heart's electrical activity. In clinical settings, it is not uncommon to accumulate data at 100 or more sites (e.g., several thousand) to generate a detailed, comprehensive map of heart chamber electrical activity. The generated detailed map may then serve as the basis for deciding on a therapeutic course of action, for example, tissue ablation as described herein, to alter the propagation of the heart's electrical activity and to restore normal heart rhythm.

Further, cardiac mapping can be generated based on detection of intracardiac electrical potential fields (e.g., which is an example of IC ECG data and/or bipolar intracardiac reference signals). A non-contact technique to simultaneously acquire a large amount of cardiac electrical information may be implemented. For example, a catheter type having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes). As another more specific example, the catheter may include other multi-spline catheters, such as five soft flexible branches, eight radial splines, or a parallel splined pancake turner type (e.g., any of which may have a total of 42 electrodes).

As example of electrical or cardiac mapping, an electrophysiological cardiac mapping system and technique based on a non-contact and non-expanded multi-electrode catheter (e.g., the catheter 110) can be implemented. ECGs may be obtained with one or more catheters 110 having multiple electrodes (e.g., such as between 42 to 122 electrodes). According to this implementation, knowledge of the relative geometry of the probe and the endocardium can be obtained by an independent imaging modality, such as transesophageal echocardiography. After the independent imaging, non-contact electrodes may be used to measure cardiac surface potentials and construct maps therefrom (e.g., in some cases using bipolar intracardiac reference signals). This technique can include the following steps (after the independent imaging step): (a) measuring electrical potentials with a plurality of electrodes disposed on a probe positioned in the heart 120; (b) determining the geometric relationship of the probe surface and the endocardial surface and/or other reference; (c) generating a matrix of coefficients representing the geometric relationship of the probe surface and the endocardial surface; and (d) determining endocardial potentials based on the electrode potentials and the matrix of coefficients.

As another example of electrical or cardiac mapping, a technique and apparatus for mapping the electrical potential distribution of a heart chamber can be implemented. An intracardiac multi-electrode mapping catheter assembly can be inserted into the heart 120. The mapping catheter (e.g., the catheter 110) assembly can include a multi-electrode array with one or more integral reference electrodes (e.g., one or the electrodes 111) or a companion reference catheter.

According to one or more exemplary embodiments, the electrodes may be deployed in the form of a substantially spherical array, which may be spatially referenced to a point on the endocardial surface by the reference electrode or by the reference catheter this is brought into contact with the endocardial surface. The preferred electrode array catheter may carry a number of individual electrode sites (e.g., at least 24). Additionally, this example technique may be implemented with knowledge of the location of each of the electrode sites on the array, as well as knowledge of the cardiac geometry. These locations are preferably determined by a technique of impedance plethysmography.

In view of electrical or cardiac mapping and according to another example, the catheter 110 can be a heart mapping catheter assembly that may include an electrode array defining a number of electrode sites. The heart mapping catheter assembly can also include a lumen to accept a reference catheter having a distal tip electrode assembly that may be used to probe the heart wall. The map heart mapping catheter assembly can include a braid of insulated wires (e.g., having 24 to 64 wires in the braid), and each of the wires may be used to form electrode sites. The heart mapping catheter assembly may be readily positionable in the heart 120 to be used to acquire electrical activity information from a first set of non-contact electrode sites and/or a second set of in-contact electrode sites.

Further, according to another example, the catheter 110 that can implement mapping electrophysiological activity within the heart can include a distal tip that is adapted for delivery of a stimulating pulse for pacing the heart or an ablative electrode for ablating tissue in contact with the tip. This catheter 110 can further include at least one pair of orthogonal electrodes to generate a difference signal indicative of the local cardiac electrical activity adjacent the orthogonal electrodes.

As noted herein, the system 100 can be utilized to detect, diagnose, and/or treat cardiac conditions. In example operation, a process for measuring electrophysiologic data in a heart chamber may be implemented by the system 100. The process may include, in part, positioning a set of active and passive electrodes into the heart 120, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

As another example operation, cardiac mapping may be implemented by the system 100 using one or more ultrasound transducers. The ultrasound transducers may be inserted into a patient's heart 120 and may collect a plurality of ultrasound slices (e.g., two dimensional or three-dimensional slices) at various locations and orientations within the heart 120. The location and orientation of a given ultrasound transducer may be known and the collected ultrasound slices may be stored such that they can be displayed at a later time. One or more ultrasound slices corresponding to the position of the probe 105 (e.g., a treatment catheter shown as catheter 110) at the later time may be displayed and the probe 105 may be overlaid onto the one or more ultrasound slices.

In view of the system 100, it is noted that cardiac arrhythmias, including atrial arrhythmias, may be of a multiwavelet reentrant type, characterized by multiple asynchronous loops of electrical impulses that are scattered about the atrial chamber and are often self-propagating (e.g., another example of the IC ECG data). Alternatively, or in addition to the multiwavelet reentrant type, cardiac arrhythmias may also have a focal origin, such as when an isolated region of tissue in an atrium fires autonomously in a rapid, repetitive fashion (e.g., another example of the IC ECG data). Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

For example, aFib occurs when the normal electrical impulses (e.g., another example of the IC ECG data) generated by the sinoatrial node are overwhelmed by disorganized electrical impulses (e.g., signal interference) that originate in the atria veins and PVs causing irregular impulses to be conducted to the ventricles. An irregular heartbeat results and may last from minutes to weeks, or even years. aFib is often a chronic condition that leads to a small increase in the risk of death often due to strokes. A line of treatment for aFib is medication that either slows the heart rate or revert the heart rhythm back to normal. Additionally, persons with aFib are often given anticoagulants to protect them from the risk of stroke. The use of such anticoagulants comes with its own risk of internal bleeding. In some patients, medication is not sufficient and their aFib is deemed to be drug-refractory, i.e., untreatable with standard pharmacological interventions. Synchronized electrical cardioversion may also be used to convert aFib to a normal heart rhythm. Alternatively, aFib patients are treated by catheter ablation.

A catheter ablation-based treatment may include mapping the electrical properties of heart tissue, especially the endocardium and the heart volume, and selectively ablating cardiac tissue by application of energy. Electrical or cardiac mapping (e.g., implemented by any electrophysiological cardiac mapping system and technique described herein) includes creating a map of electrical potentials (e.g., a voltage map) of the wave propagation along the heart tissue or a map of arrival times (e.g., a LAT map) to various located points. Electrical or cardiac mapping (e.g., a cardiac map) may be used for detecting local heart tissue dysfunction. Ablations, such as those based on cardiac mapping, can cease or modify the propagation of unwanted electrical signals from one portion of the heart 120 to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. Another example of an energy delivery technique includes irreversible electroporation (IRE), which provides high electric fields that damage cell membranes. In a two-step procedure (e.g., mapping followed by ablation) electrical activity at points within the heart 120 is typically sensed and measured by advancing the catheter 110 containing one or more electrical sensors (e.g., electrodes 111) into the heart 120 and obtaining/acquiring data at a multiplicity of points (e.g., as biometric data generally, or as ECG data specifically). This ECG data is then utilized to select the endocardial target areas, at which ablation is to be performed.

Cardiac ablation and other cardiac electrophysiological procedures have become increasingly complex as clinicians treat challenging conditions such as atrial fibrillation and ventricular tachycardia. The treatment of complex arrhythmias can now rely on the use of three-dimensional (3D) mapping systems to reconstruct the anatomy of the heart chamber of interest. In this regard, the detection engine 101 employed by the system 100 herein manipulates and evaluates the biometric data generally, or the ECG data specifically, to produce improved tissue data that enables more accurate diagnosis, images, scans, and/or maps for treating an abnormal heartbeat or arrhythmia. For example, cardiologists rely upon software, such as the Complex Fractionated Atrial Electrograms (CFAE) module of the CARTO® 3 3D mapping system, produced by Biosense Webster, Inc. (Diamond Bar, Calif.), to generate and analyze ECG data. The detection engine 101 of the system 100 enhances this software to generate and analyze the improved biometric data, which further provide multiple pieces of information regarding electrophysiological properties of the heart 120 (including the scar tissue) that represent cardiac substrates (anatomical and functional) of aFib.

Accordingly, the system 100 can implement a 3D mapping system, such as CARTO® 3 3D mapping system, to localize the potential arrhythmogenic substrate of the cardiomyopathy in terms of abnormal ECG detection. The substrate linked to these cardiac conditions is related to the presence of fragmented and prolonged ECGs in the endocardial and/or epicardial layers of the ventricular chambers (right and left). For instance, areas of low or medium voltage may exhibit ECG fragmentation and prolonged activities. Further, during sinus rhythm, areas of low or medium voltage may corresponds to a critical isthmus identified during sustained and organized ventricular arrhythmias (e.g., applies to non-tolerated ventricular tachycardias, as well as in the atria). In general, abnormal tissue is characterized by low-voltage ECGs. However, initial clinical experience in endo-epicardial mapping indicates that areas of low-voltage are not always present as the sole arrhythmogenic mechanism in such patients. In fact, areas of low or medium voltage may exhibit ECG fragmentation and prolonged activities during sinus rhythm, which corresponds to the critical isthmus identified during sustained and organized ventricular arrhythmias, e.g., applies only to non-tolerated ventricular tachycardias. Moreover, in many cases, ECG fragmentation and prolonged activities are observed in the regions showing a normal or near-normal voltage amplitude (>1-1.5 mV). Although the latter areas may be evaluated according to the voltage amplitude, they cannot be considered as normal according to the intracardiac signal, thus representing a true arrhythmogenic substrate. The 3D mapping may be able to localize the arrhythmogenic substrate on the endocardial and/or epicardial layer of the right/left ventricle, which may vary in distribution according to the extension of the main disease.

As another example operation, cardiac mapping may be implemented by the system 100 using one or more multiple-electrode catheters (e.g., the catheter 110). Multiple-electrode catheters are used to stimulate and map electrical activity in the heart 120 and to ablate sites of aberrant electrical activity. In use, the multiple-electrode catheter is inserted into a major vein or artery, e.g., femoral vein, and then guided into the chamber of the heart 120 of concern. A typical ablation procedure involves the insertion of the catheter 110 having at least one electrode 111 at its distal end, into a heart chamber. A reference electrode is provided, taped to the skin of the patient or by means of a second catheter that is positioned in or near the heart or selected from one or the other electrodes 111 of the catheter 110. Radio frequency (RF) current is applied to a tip electrode 111 of the ablating catheter 110, and current flows through the media that surrounds it (e.g., blood and tissue) toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically nonconductive. During this process, heating of the tip electrode 111 also occurs as a result of conduction from the heated tissue to the electrode itself. If the electrode temperature becomes sufficiently high, possibly above 60 degrees Celsius, a thin transparent coating of dehydrated blood protein can form on the surface of the electrode 111. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs, and the catheter 110 must be removed from the body and the tip electrode 111 cleaned.

Figure 2:
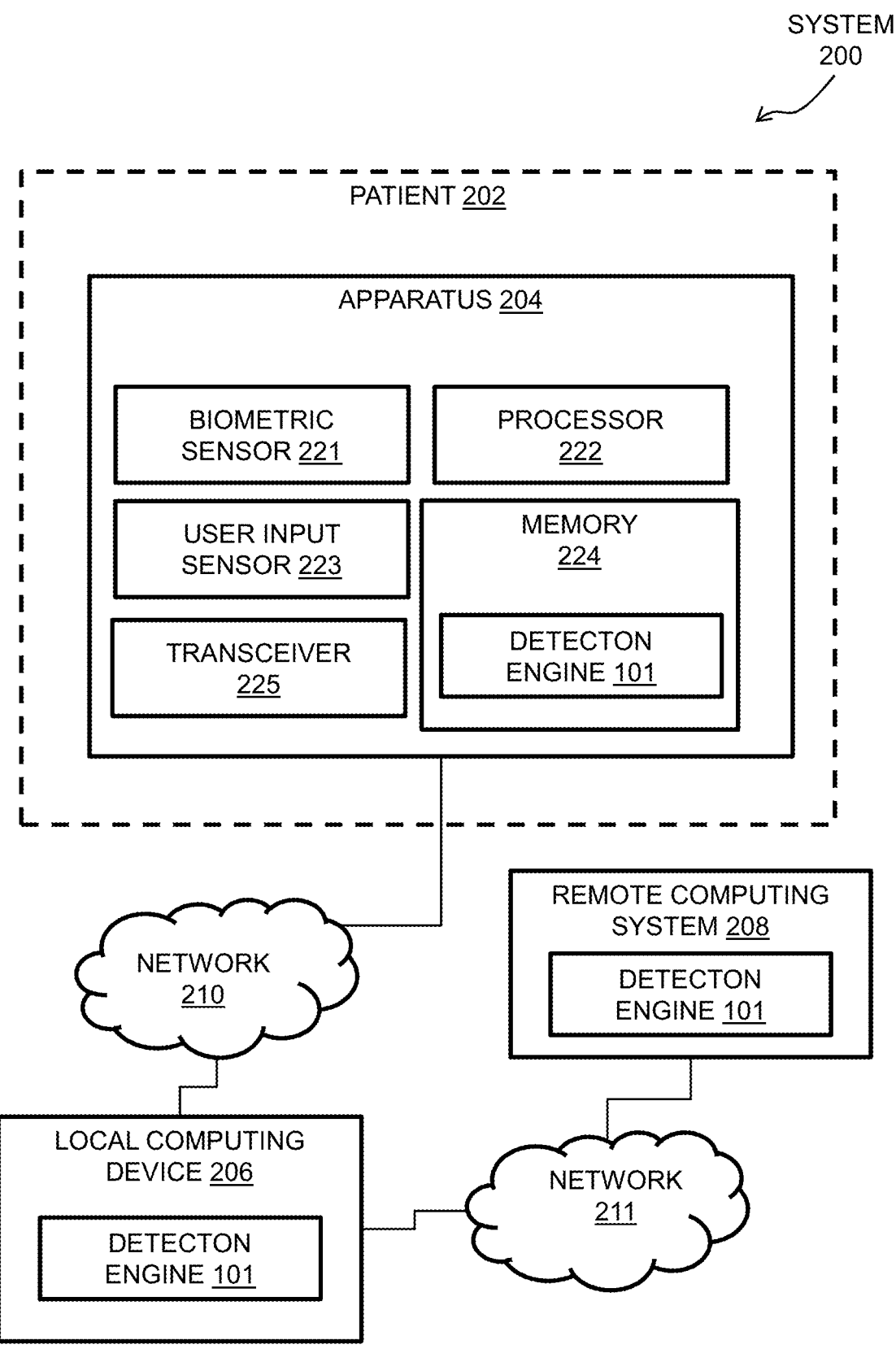
FIG. 2 illustrates a block diagram of an example system for an anatomically correct reconstruction of an atrium according to one or more embodiments.

Turning now to FIG. 2, a diagram of a system 200 in which one or more features of the disclosure subject matter can be implemented is illustrated according to one or more exemplary embodiments. The system 200 includes, in relation to a patient 202 (e.g., an example of the patient 125 of FIG. 1), an apparatus 204, a local computing device 206, a remote computing system 208, a first network 210, and a second network 211. Further, the apparatus 204 can include a biometric sensor 221 (e.g., an example of the catheter 110 of FIG. 1), a processor 222, a user input (UI) sensor 223, a memory 224, and a transceiver 225. Note that the detection engine 101 of FIG. 1 is reused in FIG. 2 for ease of explanation and brevity.

According to an embodiment, the apparatus 204 can be an example of the system 100 of FIG. 1, where the apparatus 204 can include both components that are internal to the patient and components that are external to the patient. According to another embodiment, the apparatus 204 can be an apparatus that is external to the patient 202 that includes an attachable patch (e.g., that attaches to a patient's skin). According to another embodiment, the apparatus 204 can be internal to a body of the patient 202 (e.g., subcutaneously implantable), where the apparatus 204 can be inserted into the patient 202 via any applicable manner including orally injecting, surgical insertion via a vein or artery, an endoscopic procedure, or a laparoscopic procedure. According to an embodiment, while a single apparatus 204 is shown in FIG. 2, example systems may include a plurality of apparatuses.

Accordingly, the apparatus 204, the local computing device 206, and/or the remote computing system 208 can be programed to execute computer instructions with respect the detection engine 101. As an example, the memory 223 stores these instructions for execution by the processor 222 so that the apparatus 204 can receive and process the biometric data via the biometric sensor 201. In this way, the processor 222 and the memory 223 are representative of processors and memories of the local computing device 206 and/or the remote computing system 208.

The apparatus 204, local computing device 206, and/or the remote computing system 208 can be any combination of software and/or hardware that individually or collectively store, execute, and implement the detection engine 101 and functions thereof. Further, the apparatus 204, local computing device 206, and/or the remote computing system 208 can be an electronic, computer framework comprising and/or employing any number and combination of computing device and networks utilizing various communication technologies, as described herein. The apparatus 204, local computing device 206, and/or the remote computing system 208 can be easily scalable, extensible, and modular, with the ability to change to different services or reconfigure some features independently of others.

The networks 210 and 211 can be a wired network, a wireless network, or include one or more wired and wireless networks. According to an embodiment, the network 210 is an example of a short-range network (e.g., local area network (LAN), or personal area network (PAN)). Information can be sent, via the network 210, between the apparatus 204 and the local computing device 206 using any one of various short-range wireless communication protocols, such as Bluetooth, Wi-Fi, Zigbee, Z-Wave, near field communications (NFC), ultra-band, Zigbee, or infrared (IR). Further, the network 211 is an example of one or more of an Intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information can be sent, via the network 211, using any one of various long-range wireless communication protocols (e.g., TCP/IP, HTTP, 3G, 4G/LTE, or 5G/New Radio). Note that for either network 210 and 211 wired connections can be implemented using Ethernet, Universal Serial Bus (USB), RJ-11 or any other wired connection and wireless connections can be implemented using Wi-Fi, WiMAX, and Bluetooth, infrared, cellular networks, satellite or any other wireless connection methodology.

In operation, the apparatus 204 can continually or periodically obtain, monitor, store, process, and communicate via network 210 the biometric data associated with the patient 202. Further, the apparatus 204, local computing device 206, and/the remote computing system 208 are in communication through the networks 210 and 211 (e.g., the local computing device 206 can be configured as a gateway between the apparatus 204 and the remote computing system 208). For instance, the apparatus 204 can be an example of the system 100 of FIG. 1 configured to communicate with the local computing device 206 via the network 210. The local computing device 206 can be, for example, a stationary/standalone device, a base station, a desktop/laptop computer, a smart phone, a smartwatch, a tablet, or other device configured to communicate with other devices via networks 211 and 210. The remote computing system 208, implemented as a physical server on or connected to the network 211 or as a virtual server in a public cloud computing provider (e.g., Amazon Web Services (AWS)®) of the network 211, can be configured to communicate with the local computing device 206 via the network 211. Thus, the biometric data associated with the patient 202 can be communicated throughout the system 200.

Elements of the apparatus 204 are now described. The biometric sensor 221 may include, for example, one or more transducers configured to convert one or more environmental conditions into an electrical signal, such that different types of biometric data are observed/obtained/acquired. For example, the biometric sensor 221 can include one or more of an electrode (e.g., the electrode 111 of FIG. 1), a temperature sensor (e.g., thermocouple), a blood pressure sensor, a blood glucose sensor, a blood oxygen sensor, a pH sensor, an accelerometer, and a microphone.

The processor 222, in executing the detection engine 101, can be configured to receive, process, and manage the biometric data acquired by the biometric sensor 221, and communicate the biometric data to the memory 224 for storage and/or across the network 210 via the transceiver 225. Biometric data from one or more other apparatuses 204 can also be received by the processor 222 through the transceiver 225. Also, as described in more detail herein, the processor 222 may be configured to respond selectively to different tapping patterns (e.g., a single tap or a double tap) received from the UI sensor 223, such that different tasks of a patch (e.g., acquisition, storing, or transmission of data) can be activated based on the detected pattern. In some embodiments, the processor 222 can generate audible feedback with respect to detecting a gesture.

The UI sensor 223 includes, for example, a piezoelectric sensor or a capacitive sensor configured to receive a user input, such as a tapping or touching. For example, the UI sensor 223 can be controlled to implement a capacitive coupling, in response to tapping or touching a surface of the apparatus 204 by the patient 202. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface, such that the tapping or touching of the surface activates the monitoring device.

The memory 224 is any non-transitory tangible media, such as magnetic, optical, or electronic memory (e.g., any suitable volatile and/or non-volatile memory, such as ran-dom-access memory or a hard disk drive). The memory 224 stores the computer instructions for execution by the pro-cessor 222.

The transceiver 225 may include a separate transmitter and a separate receiver. Alternatively, the transceiver 225 may include a transmitter and receiver integrated into a single device.

In operation, the apparatus 204, utilizing the detection engine 101, observes/obtains the biometric data of the patient 202 via the biometric sensor 221, stores the biometric data in the memory, and shares this biometric data across the system 200 via the transceiver 225. The detection engine 101 can then utilize models, algorithms (e.g., the deep learning optimization), neural networks, machine learning, and/or artificial intelligence to generate and provide the mappings to physician, to reduce processing loads for the system 100, and to transform operations the system 100 to more accurate mapping machines.

Figure 3:
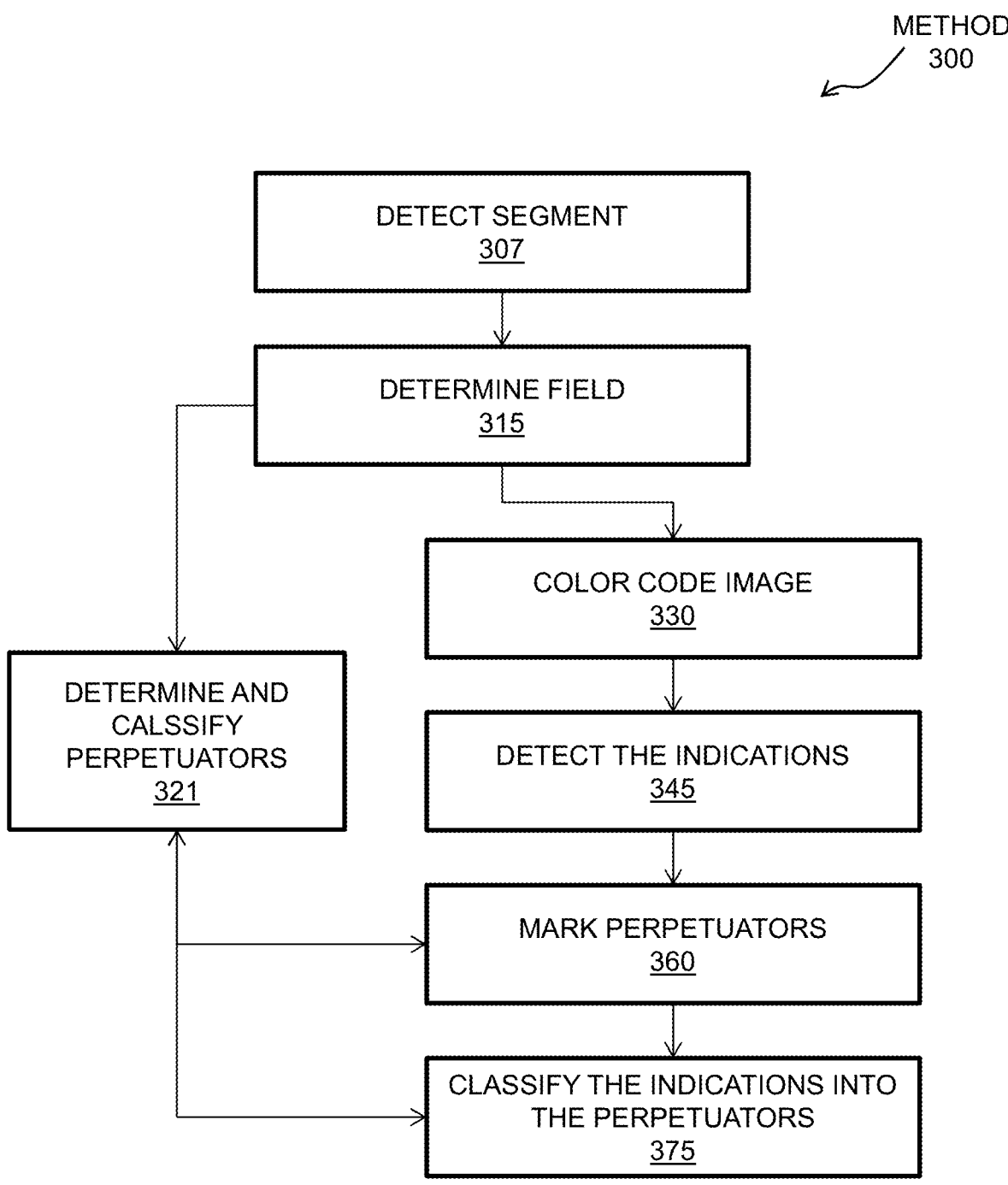
FIG. 3 illustrates a method according to one or more embodiments.

Turning now to FIG. 3, a method 300 is illustrated according to one or more embodiments. The method 300 demonstrates, in general, one or more operations of the detection engine 101 that implement a deep learning opti-mization for detecting perpetuators of aFib to be ablated for treatment of persistent aFib subject and classifying velocity vector field images and raw data into the perpetuators.

The method 300 begins at block 307, where the detection engine 101 detects one or more segments of LATs (e.g., relative to a first activation time). In this regard, inputs to the detection engine 101 include biometric data in the form of ECG data signals. From the ECG data signals one or more of LATs are determined across at least one time interval (e.g., a segment). Specifically, detection engine 101 deter-mines a point in time of a threshold activity corresponding to a local activation, calculated based on a normalized initial starting point (e.g., relative to a first activation time).

At block 315, the detection engine 101 calculates a field, such as by modeling a vector velocity field. For instance, a vector velocity field that measures and quantifies an instan-taneous velocity of ECG data signals as they pass through the LAT (e.g., by calculating a direction of an electrical wave at each x, y point and utilizing a derivative of a polynomial surface to provide the velocity vector field). According to one or more embodiments, the catheter 110 can be located on a surface of an atria (x, y) plane, and the detection engine 101 can use a scatter plot to describe the LAT (e.g., relative to a first activation time). The detection engine 101 can estimate coefficients of the scatter plot and determine a derivative thereof to provide the velocity vector field.

At block 321, the detection engine 101 to detect and classify perpetuators. In this regard, the detection engine 101 utilizes the velocity vector fields of block 315 as an input to a machine learning and/or artificial intelligence algorithm (e.g., a deep convolutional neural network) to detect loca-tions of "gold standard" perpetuators. One or more advan-tages, technical effects, and/or benefits of the block 321 includes a big data effort that renders an understanding of specific case outcomes, which includes whether an outcome of an ablation was successful or not (e.g., whether an ablation treatment had one or more positive and negative outcomes and to what degree). Therefore, the detection engine 101 provides an automatic understanding from a set of ECG signals that can be displayed via a GUI. The, the detection engine 101 executing the method 300 can provide a retrospective analysis that investigates past cases and determines where ablation occurred, as well as provide a prospective analysis to determine where to ablate in future cases.

According to one or more embodiments, the detection engine 101 utilizes a machine learning algorithm, such as a neural network as described herein, to determine cues in the ECG data signals as to the outcome (e.g., which portion of the data indicate when and if a procedure had a positive outcome). The cues can also include, but are not limited to, utilizing inputs such as a system state, parameters of an ablation, ablation locations, ablation duration, applied force, power, and temperature. Once tachycardia has changed due to ablation and is maintained, which includes, for example and elongation then breakdown of the tachycardia, the machine learning algorithm of the detection engine 101 can automatically tag an event and/or a location that caused termination. The machine learning algorithm of the detec-tion engine 101 may further tag physician provided locations and events that indicate the ablation resolved in termination as predicted/expected by the machine learning algorithm. Thus, the detection engine 101 makes users aware of clinical outcomes of electrophysiology procedures. Additionally, operations of the detection engine 101 can be applied to other features of interest, such as HIS Bundle (e.g., includ-ing special localized signals) and phrenic capture (e.g., including data frag stimulus during AI session), and an understanding of an appearance of a successful termination.

Figure 4:
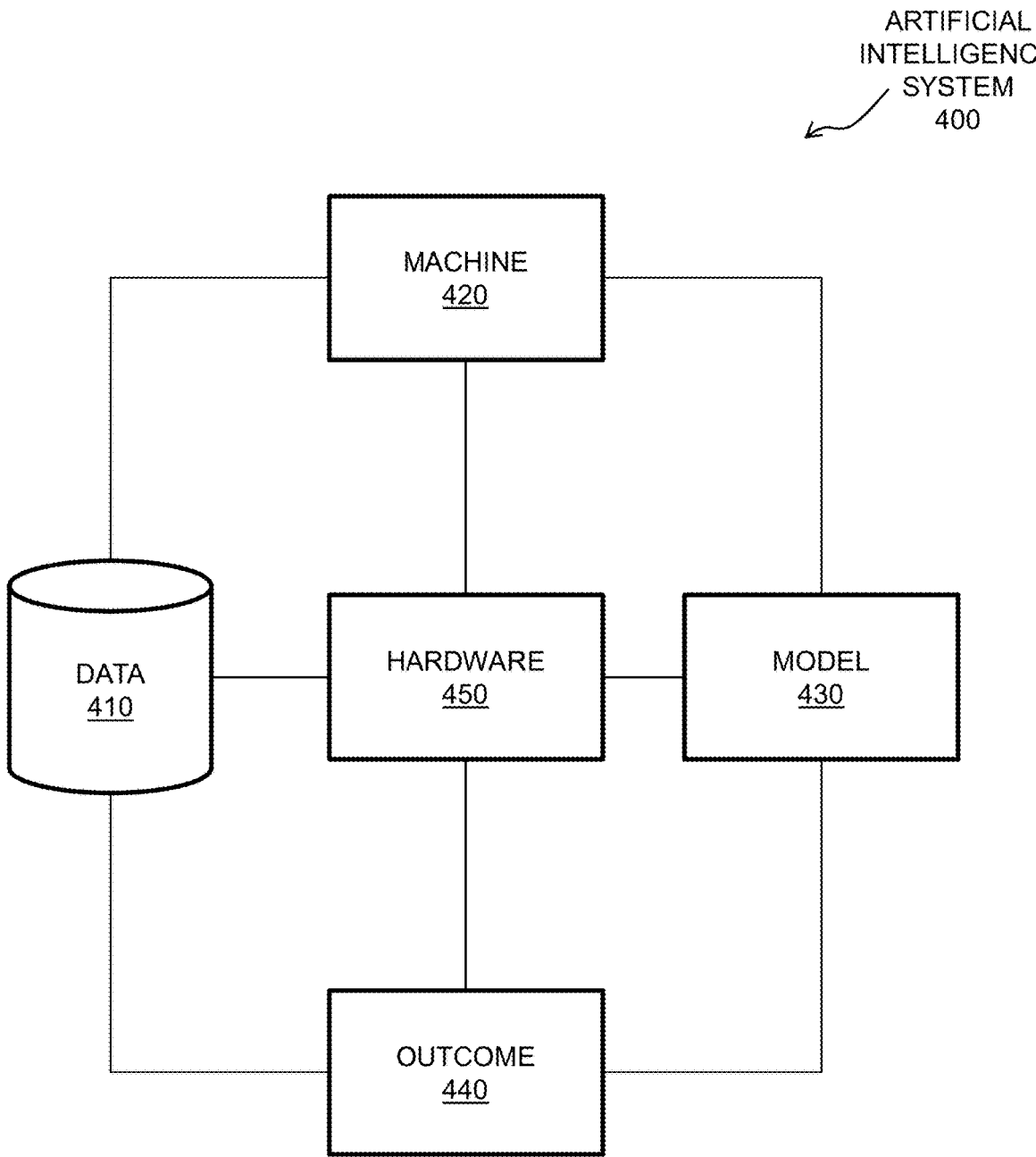
FIG. 4 illustrates a graphical depiction of an artificial intelligence system according to one or more exemplary embodiments.
Figure 5:
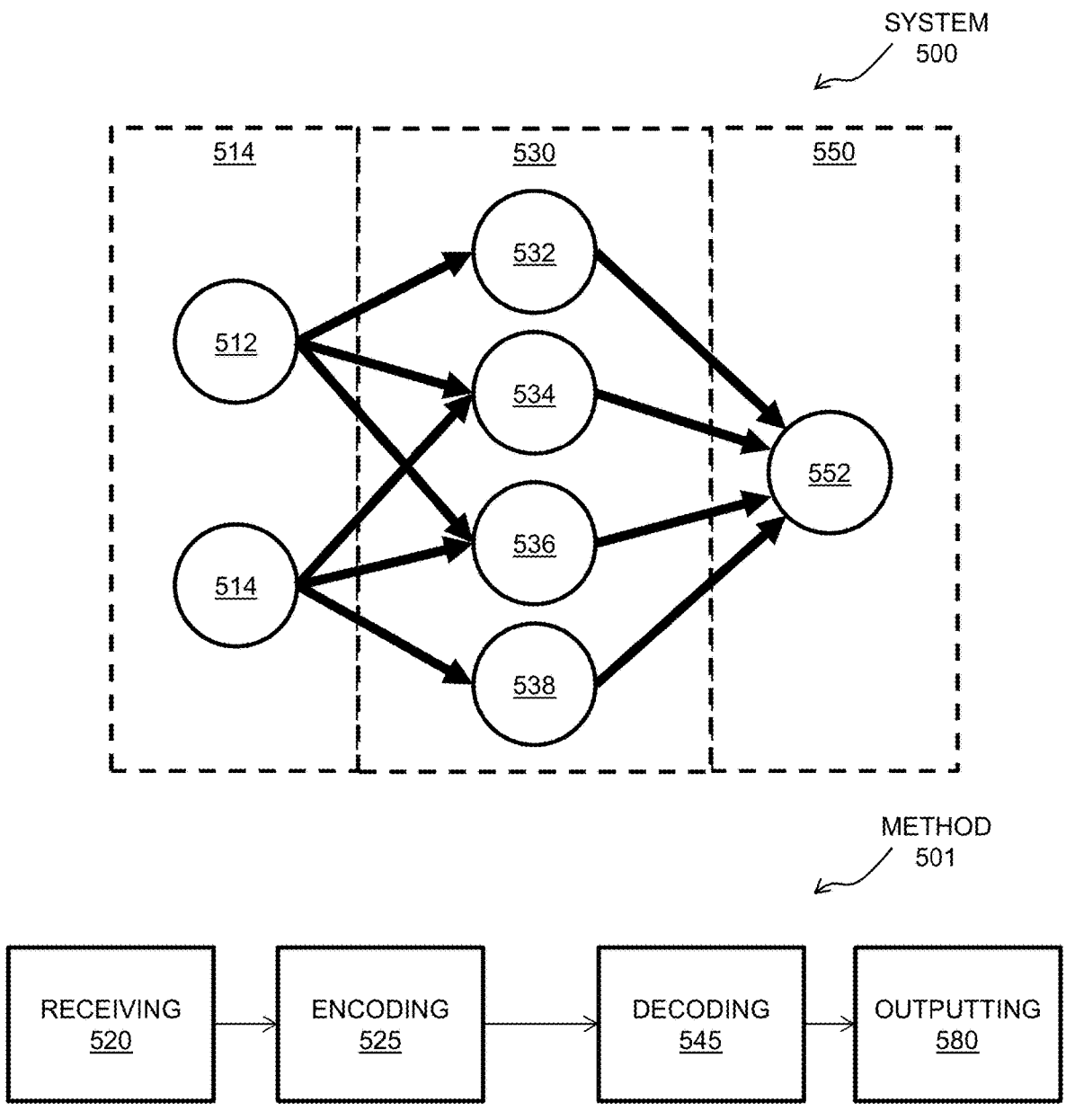
FIG. 5 illustrates an example of a neural network and a block diagram of a method performed in the neural network according to one or more embodiments.

In connection with block 321 of the method 300, FIG. 4 illustrates a graphical depiction of an artificial intelligence system 400 according to one or more embodiments. The artificial intelligence system 400 includes data 410 (e.g., biometric data), a machine 420, a model 430, an outcome 440, and (underlying) hardware 450. The description of FIGS. 4-5 is made with reference to FIGS. 1-3 for ease of understanding where appropriate. For example, the machine 410, the model 430, and the hardware 450 can represent aspects of the detection engine 101 of FIGS. 1-2 (e.g., machine learning and/or an artificial intelligence algorithm therein), while the hardware 450 can also represent the catheter 110 of FIG. 1, the console 160 of FIG. 1, and/o the apparatus 204 of FIG. 2. In general, the machine learning and/or the artificial intelligence algorithms of the artificial intelligence system 400 (e.g., as implemented by the detec-tion engine 101 of FIGS. 1-2) operate with respect to the hardware 450, using the data 410, to train the machine 420, build the model 430, and predict the outcomes 440.

For instance, the machine 420 operates as the controller or data collection associated with the hardware 450 and/or is associated therewith. The data 410 (e.g., the biometric data as described herein) can be on-going data or output data associated with the hardware 450. The data 410 can also include currently collected data, historical data, or other data from the hardware 450; can include measurements during a surgical procedure and may be associated with an outcome of the surgical procedure; can include a temperature of the heart 140 of FIG. 1 collected and correlated with an outcome of a heart procedure; and can be related to the hardware 450. The data 410 can be divided by the machine 420 into one or more subsets.

Further, the machine 420 trains, such as with respect to the hardware 450. This training can also include an analysis and correlation of the data 410 collected. According to one or more embodiments, the detection engine 101 can train a machine learning algorithm with respect to determining acute arrhythmia termination, aFib termination, or for any tachycardia termination and/or to identifying an outcome after a blanking period of a number of days, as well as notifying uses of long-term follow-up may be used.

For example, in the case of the heart, the data 410 of temperature and outcome may be trained to determine if a correlation or link exists between the temperature of the heart 140 of FIG. 1 during the heart procedure and the outcome. In accordance with another embodiment, training the machine 420 can include self-training by the detection engine 101 of FIG. 1 utilizing the one or more subsets. In this regard, the detection engine 101 of FIG. 1 learns to detect case classifications on a point by point basis.

Moreover, the model 430 is built on the data 410 associated with the hardware 450. Building the model 430 can include physical hardware or software modeling, algorithmic modeling, and/or the like that seeks to represent the data 410 (or subsets thereof) that has been collected and trained. In some aspects, building of the model 430 is part of self-training operations by the machine 420. The model 430 can be configured to model the operation of hardware 450 and model the data 410 collected from the hardware 450 to predict the outcome 440 achieved by the hardware 450. Predicting the outcomes 440 (of the model 430 associated with the hardware 450) can utilize a trained model 430. For example and to increase understanding of the disclosure, in the case of the heart, if the temperature during the procedure that is between 36.5 degrees Celsius and 37.89 degrees Celsius (i.e., 97.7 degrees Fahrenheit and 100.2 degrees Fahrenheit) produces a positive result from the heart procedure, the outcome 440 can be predicted in a given procedure using these temperatures. Thus, using the outcome 440 that is predicted, the machine 420, the model 430, and the hardware 450 can be configured accordingly.

Thus, for the artificial intelligence system 400 to operate with respect to the hardware 450, using the data 410, to train the machine 420, build the model 430, and predict the outcomes 440, the machine learning and/or the artificial intelligence algorithms therein can include neural networks. In general, a neural network is a network or circuit of neurons, or in a modern sense, an artificial neural network (ANN), composed of artificial neurons or nodes or cells.

For example, an ANN involves a network of processing elements (artificial neurons) which can exhibit complex global behavior, determined by the connections between the processing elements and element parameters. These connections of the network or circuit of neurons are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1. In most cases, the ANN is an adaptive system that changes its structure based on external or internal information that flows through the network.

In more practical terms, neural networks are non-linear statistical data modeling or decision-making tools that can be used to model complex relationships between inputs and outputs or to find patterns in data. Thus, ANNs may be used for predictive modeling and adaptive control applications, while being trained via a dataset. Note that self-learning resulting from experience can occur within ANNs, which can derive conclusions from a complex and seemingly unrelated set of information. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data (e.g., the biometric data) or task (e.g., monitoring, diagnosing, and treating any number of various diseases) makes the design of such functions by hand impractical.

Neural networks can be used in different fields. Thus, for the artificial intelligence system 400, the machine learning and/or the artificial intelligence algorithms therein can include neural networks that are divided generally according to tasks to which they are applied. These divisions tend to fall within the following categories: regression analysis (e.g., function approximation) including time series prediction and modeling; classification including pattern and sequence recognition; novelty detection and sequential decision making; data processing including filtering; clustering; blind signal separation, and compression. For example, Application areas of ANNs include nonlinear system identification and control (vehicle control, process control), game-playing and decision making (backgammon, chess, racing), pattern recognition (radar systems, face identification, object recognition), sequence recognition (gesture, speech, handwritten text recognition), medical diagnosis and treatment, financial applications, data mining (or knowledge discovery in databases, "KDD"), visualization and e-mail spam filtering. For example, it is possible to create a semantic profile of patient biometric data emerging from medical procedures.

According to one or more embodiments, the neural network can implement a long short-term memory neural network architecture, a convolutional neural network (CNN) architecture, or recurrent neural network (RNN) architecture other the like. The neural network can be configurable with respect to a number of layers, a number of connections (e.g., encoder/decoder connections), a regularization technique (e.g., dropout); and an optimization feature.

The long short-term memory neural network architecture includes feedback connections and can process single data points (e.g., such as images), along with entire sequences of data (e.g., such as speech or video). A unit of the long short-term memory neural network architecture can be composed of a cell, an input gate, an output gate, and a forget gate, where the cell remembers values over arbitrary time intervals and the gates regulate a flow of information into and out of the cell.

The CNN architecture is a shared-weight architecture with translation invariance characteristics where each neuron in one layer is connected to all neurons in the next layer. The regularization technique of the CNN architecture can take advantage of the hierarchical pattern in data and assemble more complex patterns using smaller and simpler patterns. If the neural network implements the CNN architecture, other configurable aspects of the architecture can include a number of filters at each stage, kernel size, and a number of kernels per layer.

Turning now to FIG. 5, an example of a neural network 500 and a block diagram of a method 501 performed in the neural network 500 are shown according to one or more embodiments. The neural network 500 operates to support implementation of the machine learning and/or the artificial intelligence algorithms (e.g., as implemented by the detection engine 101 of FIGS. 1-2) described herein. The neural network 500 can be implemented in hardware, such as the machine 420 and/or the hardware 450 of FIG. 4. As indicated herein, the description of FIGS. 4-5 is made with reference to FIGS. 1-3 for ease of understanding where appropriate.

In an example operation, the detection engine 101 of FIG. 1 includes collecting the data 410 from the hardware 450. In the neural network 500, an input layer 510 is represented by a plurality of inputs (e.g., inputs 512 and 514 of FIG. 5). With respect to block 520 of the method 501, the input layer 510 receives the inputs 512 and 514. The inputs 512 and 514 can include biometric data. For example, the collecting of the data 410 can be an aggregation of biometric data (e.g., BS ECG data, IC ECG data, and ablation data, along with catheter electrode position data), from one or more procedure recordings of the hardware 450 into a dataset (as represented by the data 410).

At block 525 of the method 501, the neural network 500 encodes the inputs 512 and 514 utilizing any portion of the data 410 (e.g., the dataset and predictions produced by the artificial intelligence system 400) to produce a latent representation or data coding. The latent representation includes one or more intermediary data representations derived from the plurality of inputs. According to one or more embodiments, the latent representation is generated by an element-wise activation function (e.g., a sigmoid function or a rectified linear unit) of the detection engine 101 of FIG. 1. As shown in FIG. 5, the inputs 512 and 514 are provided to a hidden layer 530 depicted as including nodes 532, 534, 536, and 538. The neural network 500 performs the processing via the hidden layer 530 of the nodes 532, 534, 536, and 538 to exhibit complex global behavior, determined by the connections between the processing elements and element parameters. Thus, the transition between layers 510 and 530 can be considered an encoder stage that takes the inputs 512 and 514 and transfers it to a deep neural network (within layer 530) to learn some smaller representation of the input (e.g., a resulting the latent representation).

The deep neural network can be a CNN, a long short-term memory neural network, a fully connected neural network, or combination thereof. The inputs 512 and 514 can be intracardiac ECG, body surface ECG, or intracardiac ECG and body surface ECG. This encoding provides a dimensionality reduction of the inputs 512 and 514. Dimensionality reduction is a process of reducing the number of random variables (of the inputs 512 and 514) under consideration by obtaining a set of principal variables. For instance, dimensionality reduction can be a feature extraction that transforms data (e.g., the inputs 512 and 514) from a high-dimensional space (e.g., more than 10 dimensions) to a lower-dimensional space (e.g., 2-3 dimensions). The technical effects and benefits of dimensionality reduction include reducing time and storage space requirements for the data 410, improving visualization of the data 410, and improving parameter interpretation for machine learning. This data transformation can be linear or nonlinear. The operations of receiving (block 520) and encoding (block 525) can be considered a data preparation portion of the multi-step data manipulation by the detection engine 101.

At block 545 of the method 510, the neural network 500 decodes the latent representation. The decoding stage takes the encoder output (e.g., the resulting the latent representation) and attempts to reconstruct some form of the inputs 512 and 514 using another deep neural network. In this regard, the nodes 532, 534, 536, and 538 are combined to produce in the output layer 550 an output 552, as shown in block 560 of the method 510. That is, the output layer 590 reconstructs the inputs 512 and 514 on a reduced dimension but without the signal interferences, signal artifacts, and signal noise. Examples of the output 552 include cleaned biometric data (e.g., clean/denoised version of IC ECG data or the like). The technical effects and benefits of the cleaned biometric data include enabling more accurate monitor, diagnosis, and treatment any number of various diseases.

Returning to FIG. 3, the method 300 continues at block 330, where the detection engine 101 determines/calculates codes for each point in (x, y) plane to one of four (4) directions (e.g., left can equal red, right can equal green, up can equal blue, and down can equal yellow) to provide a color code vector field image. The color code vector field image can enable focal sources or perpetuations to be located.

At block 345, the detection engine 101 detects focal/rotor indications, for example, by using a kernel (e.g., typically circle with radius of 1 mm) to scan the color coded vector field image of block 330. Generally, a kernel can be a designated space within a map and can take on a desired size (e.g., a circle or square) and dimension. In some cases, a kernel can be an address of points within a map, a calculated section of a map, a calculated boarder of a map, etc. In cardiac tissues, spiral wave reentry occurs when a wavefront of electric propagation encounters functionally unexcitable tissue and rotates around it in a vortex-like fashion. In turn, a rotor indication or rotor can be a rotation center from which a 2-dimensional spiral wave of excitation rotates outward. Further, a focal indication or focal can be an arrhythmia with electrical impulses originating and confined within the atria. The focal/rotor indications can be detected if within the kernel and all directions are in order (e.g., clockwise or counterclockwise). Thus, the detection engine 101 differentiates between focal sources and rotors (e.g., active and passive) on top of modeling vector velocity field.

At block 360, the detection engine 101 marks the perpetuators. According to one or more embodiments, perpetuators are tissue triggers and/or initiators that ensure a persistence of aFib. The detection engine 101 can automatically identify or annotate aFib perpetuators based on vector velocity and ablation information. More particularly, the detection engine 101 can determine one or more gold standard annotations of aFib perpetuators (e.g., most accurate annotation). Alternatively, or in conjunction, a physician can mark suspected perpetuators that may be ablated during an ablation procedure.

At block 375, the detection engine 101 classifies the focal/rotor indications into the perpetuators. Classifying the focal/rotor indications into the perpetuators includes classifying active or passive region of interests (ROIs) using a machine learning and/or artificial intelligence (e.g., logistic regression classifier, support vector machines, deep learning, etc.) based on engineered features and vector field maps. For example, the vector velocity images with gold standard annotations for perpetuators can be used as inputs and/or targets for neural network (e.g., an RNN or CNN as described herein) to predict if a pixel in a vector velocity image is a perpetuator. Further, classifying the one or more focal and/or rotors indications into the perpetuators can utilize velocity vector fields as an input to neural network (e.g., an RNN or CNN as described herein) used to detect locations of the gold standard perpetuators.

According to one or more embodiments, ROI annotations may be used by the detection engine 101, with respect to active, passive, and unknown categories. For example, an active ROI can indicate that the ROI was ablated and aFib was terminated or cycle length (CL) was increased due to ablation session. The active ROI includes perpetuators with "clinical value" that include an evidence that an ablation session in a vicinity of the focal/rotor caused a cycle length prolongation or atrial fibrillation termination. A passive ROI can indicate that there is no visible change in aFib characteristics that include an ablation session in the vicinity of a focal source without any visible change in atrial fibrillation characteristics. An unknown annotation of the ROI can indicate that there is no visible ablation session in the vicinity of the focal/rotor. In this way, one or more advantages, technical effects, and/or benefits of the detection engine include addressing most points of a mapping, which are not addressed by physician because the physician does not know active or passive natures of the ROI. The detection engine 101 can further assign probabilities across the active, passive, and unknown categories (e.g., a scale of 0 to 100 indicate a likelihood for a category).

Note that with respect to the operations of blocks 321, 360, and 375, the detector engine 101 can utilize the results of any operation as a feedback or input to another operation, as shown by the double arrows.

Figure 6:
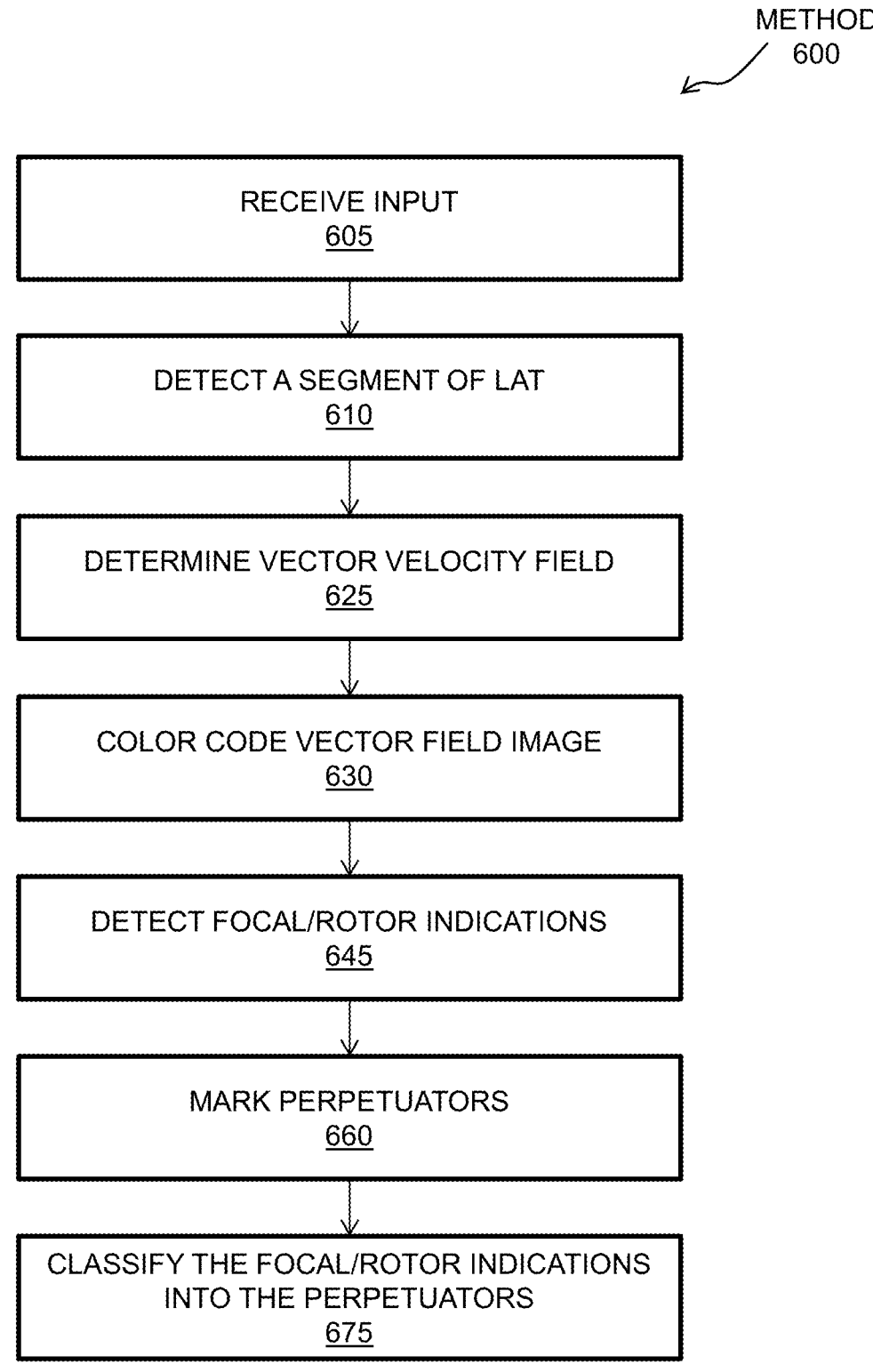
FIG. 6 illustrates a method according to one or more embodiments.

Turning now to FIG. 6, a method 600 is illustrated according to one or more embodiments. The method 600 demonstrates, in general, one or more operations of the detection engine 101 that implement an optimization for detecting perpetuators of atrial fibrillation to be ablated for treatment.

Figure 7:
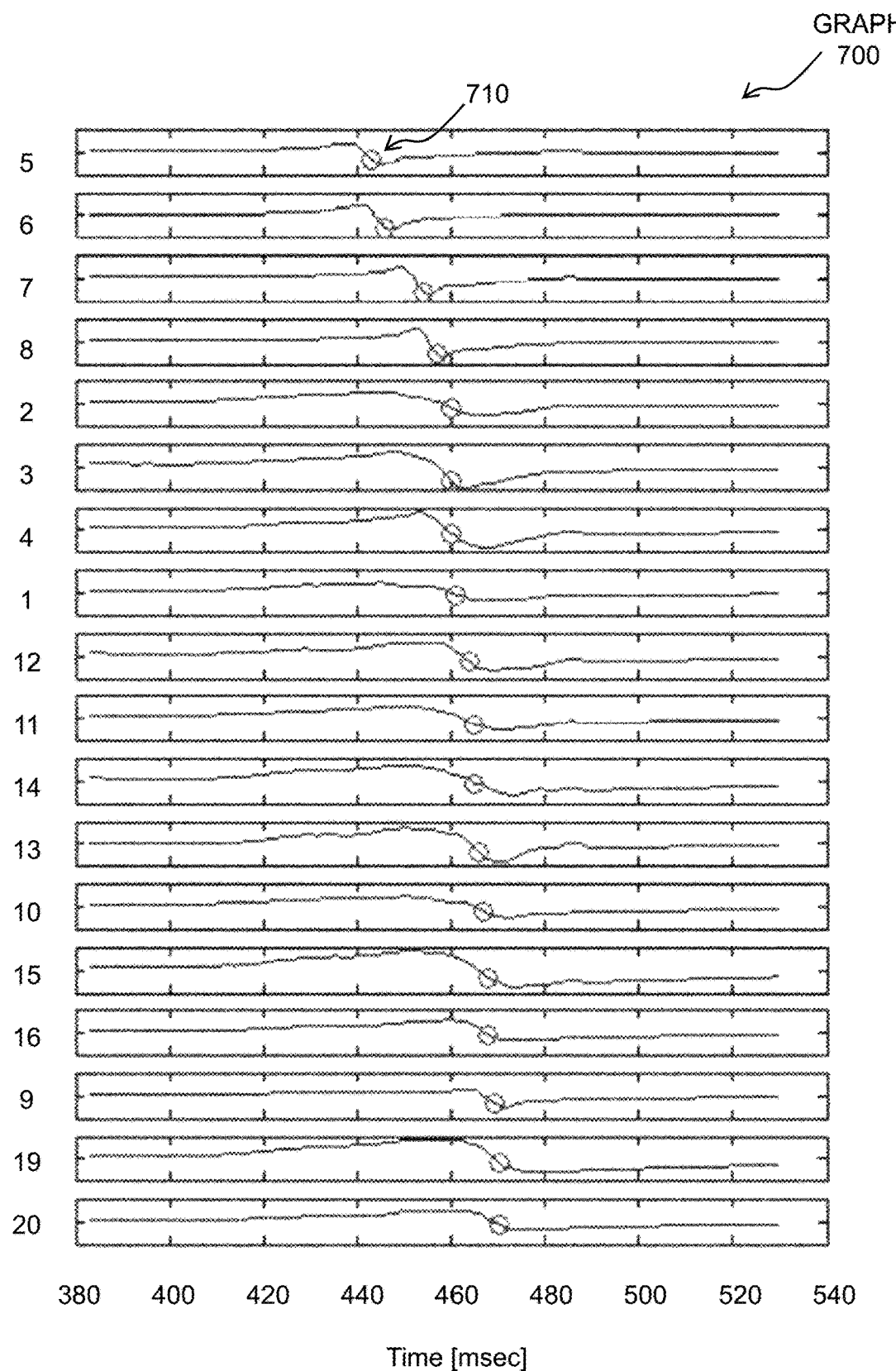
FIG. 7 illustrates a graph according to one or more embodiments.

At block 605, the method 600 begins, where the detection engine 101 receives one or more inputs, such as IC ECG data signals from a catheter 110. At block 610, the detection engine 101 detects a segment of LAT. FIG. 7 illustrates a graph 700 according to one or more embodiments. As illustrated in FIG. 7, the segments of the LAT are detected with respect to a time of activation relative to first activation times (illustrated in circles 710).

Figure 8:
FIG. 8 illustrates a graph of a surface (x, y) according to one or more embodiments.

At block 625, the detection engine 101 determines/calculates/models a vector velocity field. In this regard, the detection engine 101 assumes the catheter 110 is located on a surface of an atria (x, y) plane and uses a scatter plot to describe the time of activation (e.g., relative to the first activation time described as the circles of FIG. 7). FIG. 8 illustrates a graph 800 of a surface (x, y) according to one or more embodiments. The graph 800 provides a plot that includes the surface (x, y) and the Z msec of the activation time in a segment. Given the graph 800, the detection engine 101 can estimate coefficients of the surface (x, y) that best fit the dots thereof. The polynomial surface $T(x, y)$ can use gradient descent to estimate N and $a_{i,j}$ with respect to the cost function (as seen in Equation 1), the mean square error between L local activation time measured at position $x_s$, $y_s$, and the estimated surface $T(x_s, y_s)$ in $(x_s, y_s)$ plain is minimized with a regularization term (p typically equals 0.1)) that accounts for the number of parameters estimated in the model. More specifically, the polynomial surface may be defined Equation 2.

$$J = \sum_{s=1}^{L} [LAT(x_s, y_s) - T(x_s, y_s)]^2 + \rho N^2 \qquad \text{Equation 1}$$

$$T(x, y) = \sum_{i,j=0}^{N} a_{i,j} * x^i * y^j \qquad \text{Equation 2}$$

From $T(x, y)$ to vector fields, a model may be used to calculate the direction of the electrical wave at each point in (x, y) as defined by Equation 3.

$$V_e = \left| \begin{array}{c} \dfrac{T_x}{T_x^2 + T_y^2} \\[2mm] \dfrac{T_y}{T_x^2 + T_y^2} \end{array} \right| \qquad \text{Equation 3}$$

$T_x$ is defined by Equation 4.

$$T_x = \frac{\delta T(x, y)}{\delta x}, T_{yx} = \frac{\delta T(x, y)}{\delta y} \qquad \text{Equation 4}$$

Figure 9:
FIG. 9 illustrates a graph of velocity vector field of the surface (x, y) of FIG. 8 according to one or more embodiments.
Figure 9:
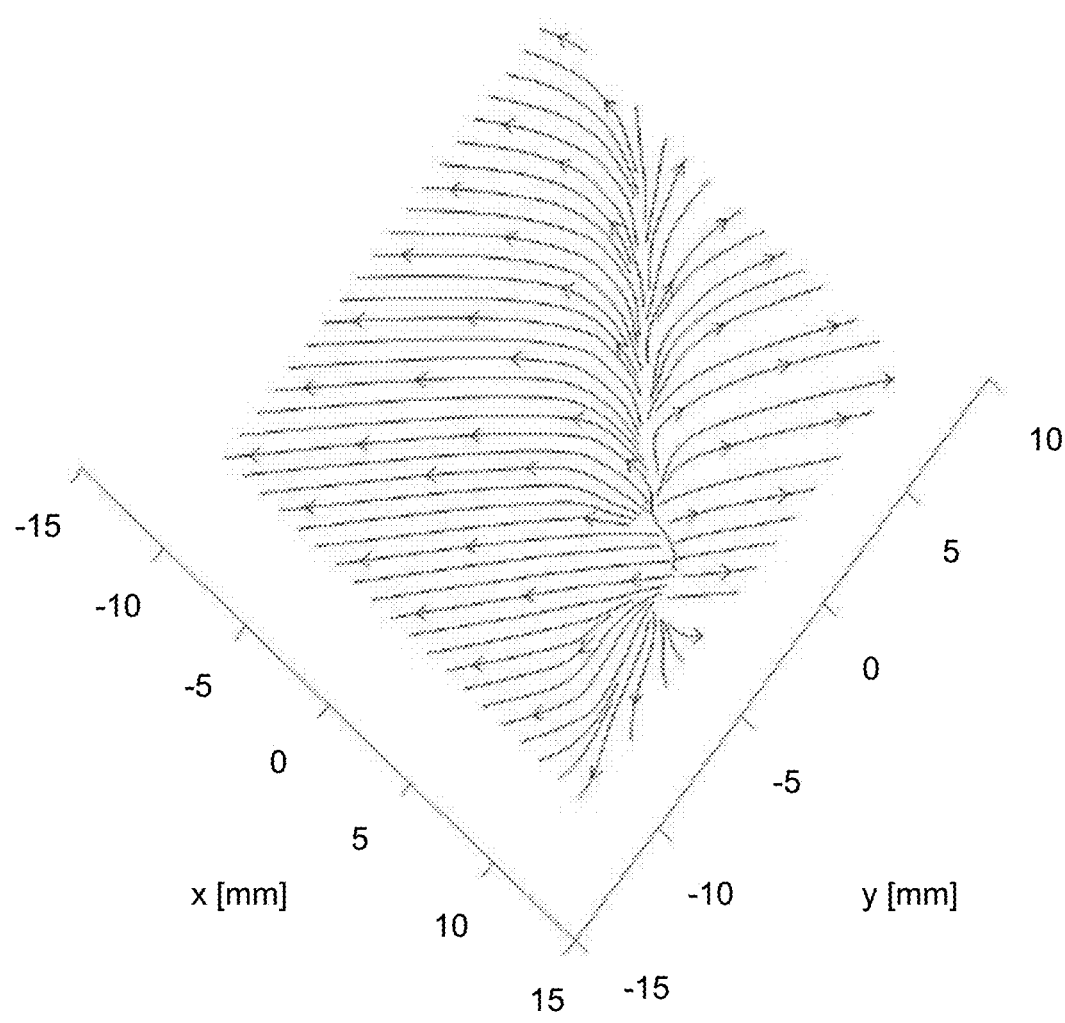

FIG. 9 illustrates a graph 900 of velocity vector field of the surface (x, y) of FIG. 8 according to one or more embodiments. That is, the derivative of the polynomial surface of FIG. 8 provides the velocity vector field illustrated in FIG. 9.

At block 630, each point in (x, y) plane is coded to one of four (4) directions to provide a color code vector field image, such that the focal source or perpetuation can be located.

At block 645, the focal/rotor can be detected by the detection engine 101. For example, the detection engine 101 can use a kernel (typically circle with radius of 1 mm) to scan the color coded vector field image obtained in block 630. Rotor/Focal points are detected if within the kernel and all 4 directions appear in order (clockwise or counterclockwise).

At block 660, the perpetuators can be marked by the detection engine 101. At block 675, the focal/rotor indications may be classified into perpetuators by the detection engine 101.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for improving efficacy of a cardiac ablation procedure, the method comprising:

obtaining, from a mapping catheter within a heart of a patient, electrocardiogram data signals including intracardiac electrograms during the cardiac ablation procedure;

modeling a velocity vector field by fitting a polynomial surface T(x,y) to local activation time values at electrode locations, applying regularization, and computing, for each location, a two-dimensional velocity vector as a spatial derivative of T(x,y);

determining, for each point in a plane, a directional code selected from directional codes (left, right, up, down) according to respective signs of x- and y-components of the velocity vector field, and forming a color coded vector field image;

detecting focal and rotor indications by scanning the color coded vector field image with a circular kernel, wherein a rotor indication is detected when the directional codes within the circular kernel occur in a clockwise or counter-clockwise circular order around the circular kernel, and a focal indication is detected when the directional codes within the kernel point appear in order;

classifying the focal and the rotor indications into perpetuators based on the velocity vector field and ablation information collected during the cardiac ablation procedure, wherein an active perpetuator is a location at which ablation causes termination of atrial fibrillation or a cycle length prolongation exceeding a threshold, a passive perpetuator is a location at which ablation causes no visible change, and an unknown perpetuator is a location at which nearby ablation has not been performed; and configuring, during the cardiac ablation procedure, one or more parameters of a surgical console that performs the cardiac ablation procedure, including at least one of power, duration, and contact force, based on the perpetuators.

2. The method of claim 1, further comprising:

detecting one or more segments of the local activation time values relative to a first activation time.

3. The method of claim 1, wherein the modeling includes calculating a direction of an electrical wave at each x, y point and utilizing a derivative of the polynomial surface to provide the velocity vector field.

4. The method of claim 1, wherein the perpetuators are classified by utilizing the velocity vector field as an input to a machine learning or artificial intelligence algorithm.

5. The method of claim 4, wherein the machine learning or the artificial intelligence algorithm comprises a deep convolutional neural network or a recurrent neural network to detect locations of gold standard perpetuators of the perpetuators.

6. The method of claim 4, wherein the machine learning or the artificial intelligence algorithm includes data identifying whether a prior cardiac ablation was successful on a respective patient.

7. The method of claim 1, further comprising: annotating atrial fibrillation perpetuators based on the vector velocity field and the ablation information.

8. The method of claim 1, wherein fitting the polynomial surface comprises minimizing a cost function that includes an L2 regularization term and performing gradient descent to obtain T(x,y), and wherein the velocity vector field is a gradient of T(x,y).

9. The method of claim 1, wherein the circular kernel has a radius of about 1 millimeter.

10. The method of claim 1, wherein classifying includes training a machine-learning model using labels derived from termination or cycle length prolongation as gold-standard outcomes.

11. A system for improving efficacy of a cardiac ablation procedure, the system comprising:

a memory; and one or more processors that are communicatively coupled to the memory, wherein the one or more processors are collectively configured to:

obtain, from a mapping catheter within a heart of a patient, electrocardiogram data signals comprising intracardiac electrograms during the cardiac ablation procedure;

model a velocity vector field by fitting a polynomial surface T(x,y) to local activation time values at electrode locations, applying regularization, and computing, for each location, a two-dimensional velocity vector as a spatial derivative of T(x,y);

determine, for each point in a plane, a directional code selected from four codes (left, right, up, down) to provide a color coded vector field image;

detect focal and rotor indications by using one or more circular kernels scan the color coded vector field image, detecting a rotor indication only upon a clockwise or counter-clockwise circular order of the directional codes within a kernel;

classify the focal and the rotor indications into perpetuators based on the velocity vector field and ablation information collected during the cardiac ablation procedure, including labeling active perpetuators by termination or cycle length prolongation after ablation; and automatically configure, during the cardiac ablation procedure, at least one of ablation power, duration, and contact force of a surgical console based on the perpetuators.

12. The system of claim 11, wherein the one or more processors are further collectively configured to:

detect one or more segments of the local activation time values relative to a first activation time.

13. The system of claim 11, wherein the velocity field is modeled by calculating a direction of an electrical wave at each x, y point and utilizing a derivative of the polynomial surface to provide the velocity vector field.

14. The system of claim 11, wherein the perpetuators are classified by utilizing the velocity vector field as an input to a machine learning or artificial intelligence algorithm.

15. The system of claim 14, wherein the machine learning or the artificial intelligence algorithm comprises a deep convolutional neural network or a recurrent neural network to detect locations of gold standard perpetuators of the perpetuators.

16. The system of claim 14, wherein the machine learning or the artificial intelligence algorithm includes data identifying whether a prior cardiac ablation was successful on a respective patient.

17. The system of claim 11, wherein the one or more processors are further collectively configured to:

automatically annotate atrial fibrillation perpetuators based on the vector velocity field and the ablation information.

18. A non-transitory computer readable medium storing instructions for improving efficacy of a cardiac ablation procedure, the instructions when executed by a surgical console that performs the cardiac ablation procedure, cause the surgical console to perform a method comprising:

obtaining, from a mapping catheter within a heart of a patient, electrocardiogram data signals comprising intracardiac electrograms during the cardiac ablation procedure;

modeling a velocity vector by fitting a polynomial surface to local activation time values with regularization and computing a two-dimensional velocity vector as a spatial derivative;

determining, for each point in a plane to provide, a four-state directional code and forming a color coded vector field image;

detecting focal and rotor indications by using circular kernels to scan the color coded vector field image, detecting a rotor indication only upon a clockwise or counter-clockwise circular order of the directional codes within a kernel;

classifying the focal and the rotor indications into perpetuators based on the velocity vector field and ablation information collected during the cardiac ablation procedure, including labeling active perpetuators by termination or cycle length prolongation after ablation; and configuring, during the cardiac ablation procedure, one or more parameters of the surgical console, including at least one of power, duration, and contact force, based on the perpetuators.

\* \* \* \* \*